United States Patent
Zheng et al.

(10) Patent No.: US 12,338,479 B2
(45) Date of Patent: Jun. 24, 2025

(54) ALDITOL OXIDASE AND APPLICATION THEREOF

(71) Applicant: SOUTH CHINA UNIVERSITY OF TECHNOLOGY, Guangzhou (CN)

(72) Inventors: Suiping Zheng, Guangzhou (CN); Shiming Tang, Guangzhou (CN); Zhiteng Zhang, Guangzhou (CN); Daocheng Liao, Guangzhou (CN); Ying Lin, Guangzhou (CN)

(73) Assignee: SOUTH CHINA UNIVERSITY OF TECHNOLOGY, Guangzhou (CN)

( * ) Notice: Subject to any disclaimer, the term of this patent is extended or adjusted under 35 U.S.C. 154(b) by 0 days.

(21) Appl. No.: 18/859,487

(22) PCT Filed: Nov. 30, 2023

(86) PCT No.: PCT/CN2023/135388
§ 371 (c)(1),
(2) Date: Oct. 23, 2024

(65) Prior Publication Data
US 2025/0115937 A1  Apr. 10, 2025

(30) Foreign Application Priority Data
Oct. 9, 2023 (CN) .......................... 202311304452.4

(51) Int. Cl.
| | |
|---|---|
| *C12P 7/40* | (2006.01) |
| *C12N 1/21* | (2006.01) |
| *C12N 9/04* | (2006.01) |
| *C12N 15/52* | (2006.01) |
| *C12R 1/19* | (2006.01) |

(52) U.S. Cl.
CPC .............. *C12P 7/40* (2013.01); *C12N 9/0006* (2013.01); *C12N 15/52* (2013.01); *C12Y 101/03041* (2013.01); *C12R 2001/19* (2021.05)

(58) Field of Classification Search
None
See application file for complete search history.

(56) References Cited

U.S. PATENT DOCUMENTS
2008/0293611 A1  11/2008  Kumar et al.

FOREIGN PATENT DOCUMENTS

| | | | |
|---|---|---|---|
| CN | 111172123 A | 5/2020 | |
| CN | 115927226 A | 4/2023 | |
| CN | 116590251 A | 8/2023 | |
| CN | 117603931 A | 2/2024 | |
| DE | 102010028008 A1 * | 10/2011 | ............... A61K 8/66 |

OTHER PUBLICATIONS

Tang et al., Substrate Promiscuity Engineering of ScALDO Enables a Versatile Minimized Enzyme Cascade for Efficient Utilization of Various Sugars, ACS Catal. 15, 2025, 1532-43. (Year: 2015).*
Sandra Gerstenbruch, Hauke Wulf, Nina MußmanAppl Microbiol Biotechnol (2012)n, Timothy O'Connell, Karl-Heinz Maurer, Uwe T. Bornscheuer—Asymmetric synthesis of D-glyceric acid by an alditol oxidase and directed evolution for enhanced oxidative activity towards glycerol—Appl Microbiol Biotechnol (2012) (Jan. 31, 2012)—Springer-Verlag 2012.
Asamizu,S.; Onaka,H.—putative xylitol oxidase [Streptomyces coelicolor]—Protein—NCBI (nih.gov)—(Dec. 25, 2021).
Zilong Wang, Xirui Li, Zhi Li—Engineering of Cascade Reactions and Alditol Oxidase for High-Yielding Synthesis of (R)-Phenylethanolamine from Styrene, I-Phenylalanine, Glycerol or Glucose—ChemCatChem 2022, 14, e202200418—(Jul. 6, 2022).

* cited by examiner

*Primary Examiner* — Todd M Epstein
(74) *Attorney, Agent, or Firm* — MUNCY, GEISSLER, OLDS & LOWE, P.C.

(57) ABSTRACT

An alditol oxidase and application thereof. The method uses D-glucose as a substrate to dock the alditol oxidase derived from *Streptomyces coelicolor* A3, and selects amino acid residues around an active center for saturation mutagenesis, and screens for alditol oxidase with D-glucose oxidizing activity by plate color development. An amino acid sequence of the alditol oxidase is shown in SEQ ID NO: 2 or SEQ ID NO: 4. The alditol oxidase has the activity of converting D-glucose to D-gluconic acid and D-glyceraldehyde to D-glyceric acid. By using the alditol oxidase, the conversion of D-glucose to pyruvic acid is realized by only three enzymes for the first time and does not depend on any coenzyme.

11 Claims, 6 Drawing Sheets
Specification includes a Sequence Listing.

```
                         SEQUENCE LISTING

Sequence total quantity: 5
SEQ ID NO: 1           moltype = AA  length = 418
FEATURE                Location/Qualifiers
source                 1..418
                       mol_type = protein
                       organism = synthetic construct
SEQUENCE: 1
MSDITVTNWA GNITYTAKEL LRPHSLDALR ALVADSARVR VLGSGHSFNE IAEPGDGGVL    60
LSLAGLPSVV DVDTAARTVR VGGGVRYAEL ARVVHARGLA LPNMASLPHI SVAGSVATGT   120
HGSGMGNGSL ASMVREVELV TADGSTVVIA RGDERFGGAV TSLGALGVVT SLTLDLEPAY   180
EMEQHVFTEL PLAGLDPATF ETVMAAAYSV SLFTDWRAPG FRQVWLKRRT DRPLDGFPYA   240
APATEKMHPV PGMPAVNCTE QFGVPGPWHE RLPHFRAEFT PSSGAELQSE YLMPREHALA   300
ALHAMDAIRE TLAPVLQTCE IRTVAADAQW LSPAYGRDTV AAHFTWVEDT AAVLPVVRRL   360
EEALVPFAAR PHWGKVFTVP AGELRALYPR LADFGALARA LDPAGKFTNA FVRGVLAG    418

SEQ ID NO: 2           moltype = AA  length = 418
FEATURE                Location/Qualifiers
source                 1..418
                       mol_type = protein
                       organism = synthetic construct
SEQUENCE: 2
MSDITVTNWA GNITYTAKEL LRPHSLDALR ALVADSARVR VLGSGHSFNE IAEPGDGGVL    60
LSLAGLPSVV DVDTAARTVR VGGGVRYAEL ARVVHARGLA LPNMASLPHI SVAGSVATGT   120
HGSGMGNGSL ASMVREVELV TADGSTVVIA RGDERFGGAV TSLGALGVVT SLTLDLEPAY   180
EMEQHVFTEL PLAGLDPATF ETVMAAAYSV SLFTDWRAPG FRQVWLKRRT DRPLDGFPYA   240
APATEKMHPV PGMPAVNCTE QFGVPGPWHE RLPHFRAEFT PSSGAELGSE YLMPREHALA   300
ALHAMDAIRE TLAPVLQTCE IRTVAADAQW LSPAYGRDTV AAHFTWVEDT AAVLPVVRRL   360
EEALVPFAAR PHWGKVFTVP AGELRALYPR LADFGALARA LDPAGKFTNA FVRGVLAG    418

SEQ ID NO: 3           moltype = DNA  length = 1257
FEATURE                Location/Qualifiers
source                 1..1257
                       mol_type = other DNA
                       organism = synthetic construct
SEQUENCE: 3
atgagcgata ttaccgtgac caactgggcg ggcaacatta cctataccgc gaaagaactg    60
ctgcgcccgc atagcctgga tgcgctgcgc gcgctggttg ccgatagcgc ccgcgtgcgc   120
gtgctgggca gcggccatag ctttaacgaa attgcggaac cgggcgatgg cggcgtgctg   180
ctgagcttag cgggcctgcc gagcgttgtg gatgttgata ccgcggcccg taccgtgcgc   240
gttggcggcg gtgttcgcta cgcggagctg gcccgcgtgg tgcacgcgcg cggcctggcg   300
ctgccgaaca tggcgagcct gccgcatatt agcgtggcgg cagcgtggc gaccggcacc   360
catggcagcg gcatgggcaa cggcagcctg gcgagcatgg tgcgcgaagt ggaactggtg   420
accgcggatg gcagcaccgt ggtgattgcg cgcggtgatg agcgctttgg cggtgcggtt   480
acgagcctgg gcgcgctggg cgtggtgacg agcttaaccc tggatctgga accggcgtat   540
gaaatggaac agcatgtgtt taccgaactg ccgctggcgg gcctggatcc ggcgacgttt   600
gaaaccgtga tggccgcggc gtatagcgtg agcctgtttta ccgattggcg cgcgccgggc   660
tttcgccaag tgtggctgaa acgccgcacc gatcgcccgc tggatggctt tccgtatgcg   720
gcgccggcga ccgaaaaaat gcatccggtg ccgggcatgc cggcggtgaa ctgcaccgaa   780
cagtttggcg tgccgggccc gtggcatgaa cgcctgccgc atttttcgcg cggaatttacc   840
ccaagtagcg gcgcggaact gggcagcgaa tatctgatgc cgcgcgaaca tgcgctggcg   900
gcgctgcatg cgatggatgc gattcgcgaa acctgcgca cggtgctgca gacctgcgaa   960
attcgcaccg tggcggccga tgcgcagtgg ctgagcccgg cgtatggccg cgataccgtg  1020
gcggcgcatt ttacctgggt ggaagatacc gcggcggtgc tgccggtggt tcgccgcctg  1080
gaagaagcgc tggtgccgtt tgcggcgcgc ccgcattggg gcaaagtgtt taccgtgccg  1140
gcgggcgaac tgcgcgcctt atatccgcgc ctggcggatt ttggcgcgct ggcgcgcgcg  1200
```

```
ttagatccgg cgggcaaatt taccaacgcg tttgtgcgcg gcgtgctggc gggctaa       1257

SEQ ID NO: 4              moltype = AA   length = 418
FEATURE                   Location/Qualifiers
source                    1..418
                          mol_type = protein
                          organism = synthetic construct
SEQUENCE: 4
MSDITVTNWA GNITYTAKEL LRPHSLDALR ALVADSARVR VLGSGHSFNE IAEPGDGGVL     60
LSLAGLPSVV DVDTAARTVR VGGGVRYAEL ARVVHARGLA LPNMASLPHI SVAGSVATGT    120
HGSGMGNGSL ASMVREVELV TADGSTVVIA RGDERFGGAV TSLGALGVVT SLTLDLEPAY    180
EMEQHVFTEL PLAGLDPATF ETVMAAAYSV SLFTDWRAPG FRQVWLKRRT DRPLDGFPYA    240
APATEKMHPV PGMPAVNCTE QFGVPGPWHE RLPHFRAEFT PSSGAELASE YLMPREHALA    300
ALHAMDAIRE TLAPVLQTCE IRTVAADAQW LSPAYGRDTV AAHFTWVEDT AAVLPVVRRL    360
EEALVPFAAR PHWGKVFTVP AGELRALYPR LADFGALARA LDPAGKFTNA FVRGVLAG      418

SEQ ID NO: 5              moltype = DNA   length = 1257
FEATURE                   Location/Qualifiers
source                    1..1257
                          mol_type = other DNA
                          organism = synthetic construct
SEQUENCE: 5
atgagcgata ttaccgtgac caactgggcg ggcaacatta cctataccgc gaaagaactg     60
ctgcgcccgc atagcctgga tgcgctgcgc gcgctggttg ccgatagcgc ccgcgtgcgc    120
gtgctgggca gcggccatag ctttaacgaa attgcggaac cgggcgatgg cggcgtgctg    180
ctgagcttag cgggcctgcc gagcgttgtg gatgttgata ccgcggcccg taccgtgcgc    240
gttggcggcg gtgttcgcta cgcggagctg gcccgcgtgg tgcacgcgcg cggcctggcg    300
ctgccgaaca tggcgagcct gccgcatatt agcgtggcgg gcagcgtggc gaccggcacc    360
catggcagcg gcatgggcaa cggcagcctg gcgagcatgg tgcgcgaagt ggaactggtg    420
accgcggatg gcagcaccgt ggtgattgcg cgcggtgatg agcgctttgg cggtgcggtt    480
acgagcctgg gcgcgctggg cgtggtgacg agcttaaccc tggatctgga accggctat    540
gaaatggaac agcatgtgtt taccgaactg ccgctggcgg gcctggatcc ggcgacgttt    600
gaaaccgtga tggccgcggc gtatagcgtg agcctgttta ccgattggcg cgcgccgggc    660
tttcgccaag tgtggctgaa acgccgcacc gatcgcccgc tggatggctt tccgtatgcg    720
gcgccggcga ccgaaaaaat gcatccggtg ccgggcatgc cggcggtgaa ctgcaccgaa    780
cagtttggcg tgccgggccc gtggcatgaa cgcctgccgc attttcgcgc ggaatttacc    840
ccaagtagcg gcgcggaact ggcgagcgaa tatctgatgc cgcgcgaaca tgcgctggcg    900
gcgctgcatg cgatggatgc gattcgcgaa accctggcgc cggtgctgca gacctgcgaa    960
attcgcaccg tggcggccga tgcgcagtgg ctgagcccgg cgtatggccg cgataccgtg   1020
gcggcgcatt ttacctgggt ggaagatacc gcggcggtgc tgccggtggt tcgccgcctg   1080
gaagaagcgc tggtgccgtt tgcggcgcgc ccgcattggg gcaaagtgtt taccgtgccg   1140
gcgggcgaac tgcgcgcctt atatccgcgc ctggcggatt ttggcgcgct ggcgcgcgcg   1200
ttagatccgg cgggcaaatt taccaacgcg tttgtgcgcg gcgtgctggc gggctaa      1257
```

ALDITOL OXIDASE AND APPLICATION THEREOF

CROSS-REFERENCE TO RELATED APPLICATIONS

This application is a national application of PCT/CN2023/135388, filed on Nov. 30, 2023, which claims priority to Chinese Patent Application No. 202311304452.4, filed on Oct. 9, 2023. The contents of all of which are incorporated herein by reference.

REFERENCE TO AN ELECTRONIC SEQUENCE LISTING

The content of the electronic sequence listing (Sequence.xml; Size: 8,964 bytes); and Date of Creation: Oct. 12, 2024) is herein incorporated by reference in its entirety.

FIELD OF TECHNOLOGY

The present application relates to the technical field of synthetic biology, and in particular to an alditol oxidase and application thereof.

BACKGROUND

Pyruvic acid, also known as 2-oxoacetic acid, is an important α-oxocarboxylic acid, colorless to light yellow. Pyruvic acid can interconvert sugars, fats and amino acids in the body through acetyl coenzyme A and the tricarboxylic acid cycle, and plays an important pivotal role in the metabolism of the three major nutrients. As an important organic acid, pyruvic acid is the precursor for the synthesis of many compounds, and has a wide range of applications in the fields of chemical industry, agriculture, medicine, food and so on.

Currently, the methods for synthesizing pyruvic acid include microbial fermentation, chemical method and multi-enzyme catalytic methods, among which the enzymatic method has attracted much attention from researchers due to its mild reaction conditions and few by-products. Natural Entner-Doudoroff pathway is an alternative pathway present in some microorganisms that lack the complete EMP pathway, and is characterized by the fact that one molecule of glucose undergoes only seven steps to obtain two molecules of pyruvic acid, which would be formed by the EMP pathway in a 10-step reaction. Sieber et al. reported an improved Entner-Doudoroff pathway in 2012 that utilizes a substrate-hybrid dehydratase (DHT) to catalyze the conversion of D-glyceric acid to pyruvic acid and D-gluconic acid to 2-keto-3-deoxy gluconic acid at the same time, eliminating phosphorylation and dephosphorylation steps in the natural Entner-Doudoroff pathway and thus reducing the number of enzymes required. Please refer to FIG. 1, an improved Entner-Doudoroff pathway uses the multi-enzyme catalytic method to synthesize pyruvic acid using D-glucose as a substrate, and the specific reaction route is as follows: D-glucose is converted to D-gluconic acid and consumes one molecule of NAD+ under catalysis of glucose dehydrogenase (GDH), followed by the conversion of one molecule of D-gluconic acid to 2-keto-3-deoxy gluconic acid by the catalysis of dehydratase (DHT). Then 2-keto-3-deoxy gluconic acid is converted to one molecule of D-glyceraldehyde and one molecule of pyruvic acid under catalysis of 2-keto-3-deoxy gluconate aldolase (KDGA), and one molecule of D-glyceraldehyde is converted to one molecule of D-glyceric acid and consumes one molecule of NAD+ under catalysis of glyceraldehyde dehydrogenase (ALDH), and one molecule of D-glyceric acid is converted to another molecule of pyruvic acid under catalysis of dehydratase (DHT). One molecule of glucose may theoretically be converted into two molecules of pyruvic acid and consume two molecules of NAD+. However, this multi-enzyme catalytic system still requires a high number of enzymes for the synthesis of pyruvic acid, and the high cost of enzyme preparation limits the large-scale application of this system, and this pathway needs to consume expensive coenzymes. Therefore, how to further design new enzyme variants to realize a new catalytic property in which one enzyme combines the functions of two enzymes, so as to reduce the number of enzymes used and eliminate the addition of coenzymes to lower the cost of the pathway, has become a key bottleneck in this field.

SUMMARY

According to an aspect of this disclosure, an alditol oxidase that simultaneously oxidizes D-glucose and D-glyceraldehyde, and an engineered strain for expressing the alditol oxidase are provided.

A first purpose of this application is to provide an alditol oxidase of which an amino acid sequence is as shown in SEQ ID NO: 2 or SEQ ID NO: 4.

Compared with the prior art, the alditol oxidase provided by this application has activity of converting D-glucose to D-gluconic acid and D-glyceraldehyde to D-glyceric acid. By using the alditol oxidase, this application realizes the conversion of D-glucose to pyruvic acid by only three enzymes for the first time, and does not depend on any coenzyme, and has great originality and application value.

A second purpose of this application is to provide a gene that encodes the alditol oxidase.

Furthermore, a nucleotide sequence of the gene is shown as SEQ ID NO: 3 or SEQ ID NO: 5.

A third purpose of this application is to provide a recombinant vector or recombinant strain containing the gene that encodes the alditol oxidase.

Furthermore, the recombinant vector uses pET28a as an expression vector.

Furthermore, the recombinant strain uses *Escherichia coli* BL21 (DE3) as a host.

A fourth purpose of this application is to provide a method for synthesizing pyruvic acid, wherein D-glucose is used as a substrate, and the pyruvic acid is synthesized through a catalytic reaction of the alditol oxidase, the dehydratase and the 2-keto-3-deoxy gluconate aldolase.

Furthermore, in the reaction system, final concentration of the glucose is 1~10 mM, the final concentration of the alditol oxidase is 0.3~0.7 mg/mL, final concentration of the dehydratase is 0.3~0.5 mg/mL, and final concentration of the 2-keto-3-deoxy gluconate aldolase is 0.1~0.3 mg/mL.

Furthermore, the reaction system further includes $MgCl_2$, Tween 20 and manganese dioxide, and reaction temperature of the reaction system is 38~42° C.

A fifth purpose of this application is to provide an application of the alditol oxidase in catalyzing oxidation of aldoses, and the aldoses are one or more of D-xylose, D-ribose, L-arabinose, D-erythrose, D-mannose, and D-galactose.

BRIEF DESCRIPTION

DETAILED DESCRIPTION

Figure 1:
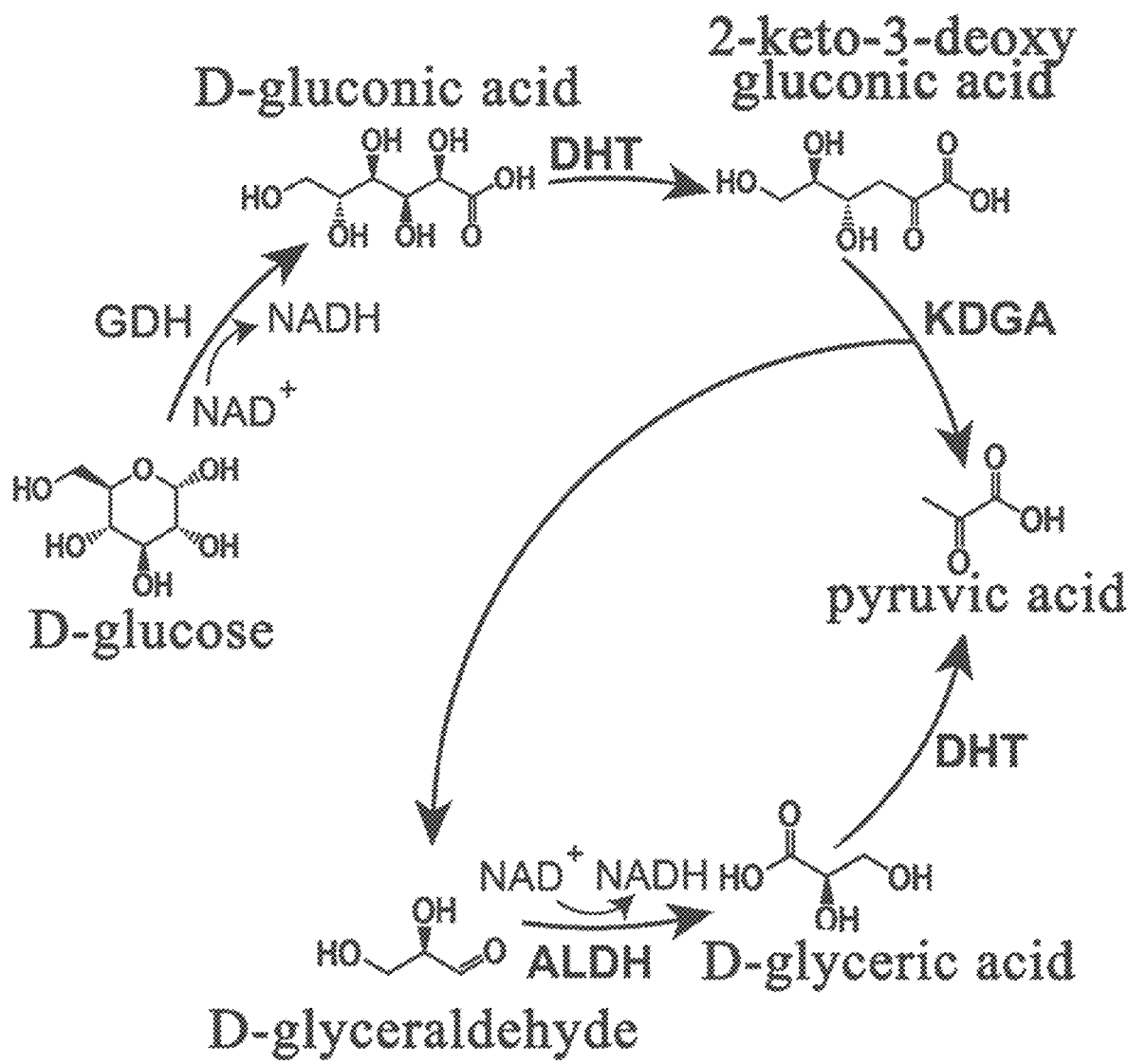
FIG. 1 is a reaction route for synthesizing pyruvic acid using D-glucose as a substrate by a multi-enzyme catalytic method in the prior art.

The present application is described in detail below with embodiments so that those skilled in the art may better understand the application and be able to carry it out, however, the scope of protection of the present invention is not limited to these embodiments only. Wherein, "amino acid substituted at original amino acid position" is used to denote the mutated amino acid in an alditol oxidase, for example, the term "AxxB" means that an amino acid at position xx is replaced by amino acid B from amino acid A of a wild-type enzyme, and position number corresponds to an amino acid sequence number of the wild-type alditol oxidase in SEQ ID No: 1.

Full gene synthesis in the embodiments of the present application were performed by Suzhou GENEWIZ Biotechnology Co., Ltd.

Materials and reagents used in the embodiments of the disclosure are commercially available materials and reagents, unless specified.

The reagents used in the embodiments of the present application are as follows:

LB medium: 10 g/L peptone, 5 g/L yeast powder, and 10 g/L NaCl were prepared with deionized water, kept at room temperature for later use after autoclaving.

TB medium: a LB medium contains 12 g/L peptone, 24 g/L yeast powder, 4 mL/L glycerol, and potassium phosphate buffer.

1M Isopropyl β-D-Thiogalactoside (IPTG) solution: 2.383 g IPTG was weighed and dissolved in deionized water, which was diluted to 10 mL after complete dissolution, and then dispensed into 2 mL preservation tube and kept frozen at −20° C. for later use Kanamycin solution (50 mg/mL): 0.5 g kanamycin sulfate was weighed and dissolved in deionized water, which was diluted to 10 mL after complete dissolution, and then dispensed into 2 mL preservation tube and kept frozen at −20° C.

In the following embodiments, the enzymes used are expressed by *Escherichia coli* BL21 (DE3), such as alditol oxidase, dehydratase (DHT), and 2-keto-3-deoxy gluconate aldolase (KDGA).

In a preferred embodiment of the application, the method of preparing the alditol oxidase in this present application includes the following steps: (1) constructing a gene of a corresponding mutation site of alditol oxidase into a pET28a expression vector to obtain a recombinant plasmid with a target enzyme gene. (2) transferring the recombinant plasmid into a host cell to obtain a corresponding engineered strain, wherein the host cell is preferably *Escherichia coli* BL21 (DE3). (3) inoculating the engineered strain into the LB medium, culturing at 37° C. overnight, then transferring to the TB medium with an initial OD value of 0.1 controlled and culturing until the OD value reaches above 0.6, then adding 0.1 mM-1 mM IPTG and culturing at 12-30° C. for 12-20 hours. (4) collecting the strain by centrifugation.

Example 1: Construction of Alditol Oxidase Genetically Engineered Strain (1) Construction of Gene Expression Vector A wild-type alditol oxidase gene (Gene ID: 1101588) from *Streptomyces coelicolor* A3 containing mutations at four sites, V125M, A244T, V133M and G399R, was obtained through NCBI, and its amino acid sequence is shown in SEQ ID NO: 1. After codon optimization of the wild-type alditol oxidase sequence, the optimized sequence was synthesized by full gene synthesis and subcloned into the gene expression vector pET28a in *Escherichia coli* to obtain a recombinant plasmid pET28a-ScALDO.

(2) Construction of BL21 (DE3) Genetically Engineered Strain for Expression of Enzymes Related to Step (1)

(21) Transformation of Recombinant Plasmid into *Escherichia Coli* Competent Cell The recombinant plasmid pET28a-ScALDO constructed in step (1) was transformed into an *Escherichia coli* expression host BL21 (DE3) by a calcium chloride method.

The BL21 (DE3) competent cell was placed on ice for 2 min in an ultra-clean bench to melt, and the recombinant plasmid, pET28a-ScALDO, was added into the BL21 (DE3) competent cell, gently blown to make them mixed evenly, and then stood on ice for 5 min, and then coated on a LB-resistant plate containing 50 mg/L kanamycin, and cultured in an incubator at 37° C. overnight.

(22) Colony PCR Identification

Positive single colonies were picked from the plates in step (21) and preliminary identification by colony PCR was carried out with 2×Utaq PCR MasterMix (Beijing Zoman Biotechnology Co., Ltd., Catalog No. ZT201A-1). A colony PCR reaction system is shown in Table 1, and a colony PCR amplification reaction program is shown in Table 2. After colony PCR amplification, a colony PCR product was spotted into the wells of 1% agarose gel electrophoresis gel (another well of DS 5000 DNA Marker was spotted as a control), and separated in an electrophoresis tank (110 V) for 30 min. After the separation, the agarose gel electrophoresis gel was immersed in Gelred staining solution for 15 min. The approximate size of colony PCR product bands was then determined in a gel imaging instrument according to the DS 5000 DNA Marker and compared with the expected band size to determine whether expression strain construction was completed. In this embodiment, positive transformants were identified by colony PCR and expression strain BL21 (DE3)/pET28a-ScALDO was obtained.

TABLE 1

| Colony PCR Reaction System | |
|---|---|
| System | Volume/μL |
| 2 × Utaq PCR MasterMix | 5 |
| Upstream Primer | 0.4 |
| Downstream primer | 0.4 |
| Single colony | — |
| Sterilized double-distilled water | 4.2 |

TABLE 2

| Colony PCR Amplification Reaction Program | | | |
|---|---|---|---|
| Program | temperature(° C.) | time | Cycle number |
| Pre-denaturation | 94 | 5 min | 1 |
| Denaturation | 94 | 30 sec | |
| Annealing | 55 | 30 sec | 30 |
| Extension | 72 | 2.5 min | |
| Extension | 72 | 10 min | 1 |
| Hold | 16 | ∞ | |

Example 2: Construction and Screening of Mutant Alditol Oxidases (1) Construction of Mutation Library of Alditol Oxidase A saturation mutation library was constructed by docking wild-type alditol oxidase (amino acid sequence shown as SEQ ID NO: 1) with D-glucose as the substrate and selecting amino acid residues around an active center for saturation mutation.

(2) Screening of Mutant Alditol Oxidases that Simultaneously Oxidizing D-Glucose and D-Glyceraldehyde The saturation mutation library was transformed into Escherichia coli BL21 (DE3) competent cells, which were subsequently coated onto a LB-resistant plate containing 50 mg/L kanamycin and cultured in an incubator at 37° C. overnight. The monoclonal colonies were screened for activity using a laboratory-developed plate coloration strategy, the basic principle of which is that the mutant alditol oxidase with catalytic activity releases $H_2O_2$ during the oxidation of the substrate glucose, and thus monoclonal colonies can be color-coded by the $H_2O_2$ coloration system for rapid identification of active mutations.

Two mutant strains with D-glucose oxidizing activity were obtained by screening, and the two mutant strains were cultured and plasmids thereof were extracted for DNA sequencing. The sequencing results showed that the mutation sites which enabled the mutant alditol oxidase to have D-glucose oxidizing activity were Q288G single mutation (corresponding to the mutation of the glutamine to glycine at position 288 of the amino acid sequence SEQ ID NO: 1) and Q288A single mutation (corresponding to the mutation of the glutamine to alanine at position 288 of the amino acid sequence SEQ ID NO: 1).

The mutant alditol oxidase containing a single mutation of Q288G was named ScALDO-Q288G, its amino acid sequence was SEQ ID NO: 2, the coding nucleotide sequence was SEQ ID NO: 3, and the corresponding expression strain was BL21 (DE3)/pET28a-ScALDO-Q288G. The mutant alditol oxidase containing a single mutation of Q288A was named ScALDO-Q288A, its amino acid sequence was SEQ ID NO: 4, the coding nucleotide sequence was SEQ ID NO: 5, and the corresponding expression strain was BL21 (DE3)/pET28a-ScALDO-Q288A.

Example 3: Construction of Genetically Engineered Strains for Dehydratase and 2-Keto-3-Deoxy Gluconate Aldolase Dehydratase gene (NCBI Reference Sequence: WP_132585145.1) from Paralcaligenes ureilyticus, and a 2-keto-3-deoxy gluconate aldolase gene (NCBI Reference Sequence: NC_005877.1) from Picrophilus torridus were obtained through literature. After codon optimization of the dehydratase and 2-keto-3-deoxy gluconate aldolase sequence, the optimized sequence was synthesized by full gene synthesis and subcloned into the gene expression vector pET28a in Escherichia coli to obtain the recombinant plasmid pET28a-PuDHT and pET28a-PtKDGA respectively.

The pET28a-PuDHT, pET28a-PtKDGA recombinant plasmids were transformed into the Escherichia coli expression host BL21 (DE3) by a calcium chloride method, respectively, and the positive transformants were identified and expression strain BL21 (DE3)/pET28a-PuDHT and BL21 (DE3)/pET28a-PtKDGA were obtained.

Example 4: Induced Expression and Purification of Enzyme

The wild-type genetically engineered strains and mutant genetically engineered strains constructed in examples 1~3, that is BL21 (DE3)/pET28a-ScALDO, BL21 (DE3)/pET28a-PuDHT, BL21 (DE3)/pET28a-PtKDGA, BL21 (DE3)/pET28a-ScALDO-Q288G, BL21 (DE3)/pET28a-ScALDO-Q288A, were inoculated into 10 mL of LB medium containing 50 mg/L kanamycin, respectively, and cultured overnight at 37° C., 250 rpm to obtain seed solutions.

The seed solutions were inoculated separately in 100 mL of TB medium containing 50 mg/L of kanamycin, and the starting $OD_{600}$ of a fermentation medium was controlled to be 0.1, and the fermentation medium was incubated at 37° C. and 220 rpm. When the fermentation medium was cultured to an $OD_{600}$ of 0.6 or more, 50 μL of 1 M IPTG was added for induction, so that the final concentration of IPTG in the fermentation medium was 0.5 mM, and the fermentation medium was placed at 16° C., 180 rpm for induction for 16 h.

After the induction, cell suspension was transferred to a 100 mL centrifuge tube and centrifuged at 6000 rpm for 5 min at room temperature; the supernatant was discarded and resuspended with sterile water, and centrifuged at 6000 rpm for 5 min at room temperature, and the supernatant was discarded. A certain volume of HEPES buffer was added to the above centrifuged bacterial precipitates respectively, which were then put into Toshiba ultrasonic crusher to sonicate for 3 s at 35% power, with an interval of 3 s, for a total of 40 min; then centrifuged at 4° C., 10,000 rpm for 30 min, to obtain crude enzyme solutions.

Purification of a target protein was carried out using an AKTA purifier and a nickel ion affinity chromatography column with an imidazole concentration of 0.3 M-0.5 M to obtain the target protein; subsequently, a desalting column was used to remove imidazole from the target protein.

Example 5: Enzyme Activity Assay of Wild-Type and Mutant Alditol Oxidases

Testing the relative activity of wild-type and mutant alditol oxidase on D-glucose: the system contained 10 mM D-glucose, 1 mM 4-AAP, 1 mM DHBS, 4 μL of horseradish peroxidase at a concentration of 0.3 g/L, and 0.1 mg/mL of wild-type or mutant alditol oxidase. The enzyme activity of ScALDO, ScALDO-Q288G and ScALDO-Q288A on D-glucose was calculated by measuring the absorbance change of the system within 5 minutes, and the relative enzyme activity was calculated when the highest enzyme activity defined as 100%.

Testing the relative activity of wild-type and mutant alditol oxidase on D-glyceraldehyde: the system contained 10 mM D-glyceraldehyde, 1 mM 4-AAP, 1 mM DHBS, 4 μL of horseradish peroxidase at a concentration of 0.3 g/L, and 0.1 mg/mL of wild-type or mutant alditol oxidase. The enzyme activity of ScALDO, ScALDO-Q288G and ScALDO-Q288A on D-glyceraldehyde was calculated by measuring the absorbance change of the system within 5 minutes, and the relative enzyme activity was calculated when the highest enzyme activity defined as 100%.

Figure 2:
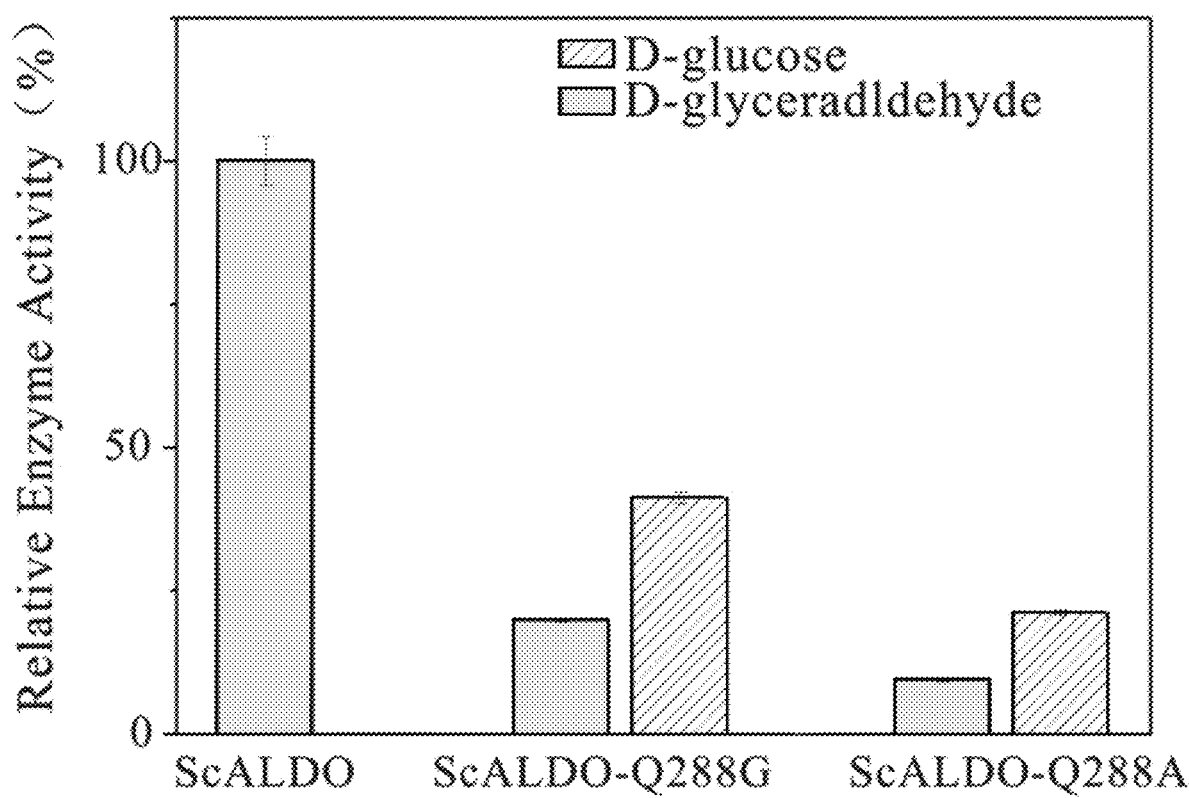
FIG. 2 shows relative enzyme activity of the alditol oxidase according to the present application for oxidizing D-glucose and D-glyceraldehyde.

Referring to FIG. 2, it shows the relative enzyme activity of the alditol oxidases of the present application for oxidizing D-glucose and D-glyceraldehyde. The wild-type alditol oxidase ScALDO does not have the activity of oxidizing D-glucose to D-glucuronic acid and has highly substrate specificity. The mutant alditol oxidases ScALDO-Q288G and ScALDO-Q288A both show obvious activity in oxidizing D-glucose to D-gluconic acid, and retain a certain activity in oxidizing D-glyceraldehyde to D-glyceric acid. Both ScALDO-Q288G and ScALDO-Q288A achieve a high level of substrate promiscuity. Apparently, the Q288G site-directed mutation and the Q288A site-directed mutation endow the wild-type alditol oxidase ScALDO with a novel property of oxidizing both D-glucose and D-glyceraldehyde. Theoretically, the alditol oxidases of the present application (ScALDO-Q288G and ScALDO-Q288A) may replace glucose dehydrogenase (GDH) and glyceraldehyde dehydrogenase (ALDH) in the synthesis pathway of glucose to pyruvic acid, reducing the number of enzymes required for synthesizing pyruvic acid from D-glucose from four to three.

Example 6: Three-Enzyme-Catalytic Reaction for Pyruvic acid Synthesis with Glucose as Substrate 5 mM glucose, 5 mM $MgCl_2$, 0.1% Tween 20, 1 g/L manganese dioxide, 0.5 mg/mL alditol oxidase (ScALDO-Q288G), 0.4 mg/mL dehydratase (PuDHT), 0.2 mg/mL 2-keto-3-deoxy gluconate aldolase (PtKDGA) were added into the reaction system, and the system reacted for 24 hours, in which 0.5 g/L manganese dioxide was added at 2 hours and 4 hours respectively. The reaction temperature of the reaction system was 40° C., the reaction pH was 8.0, the buffer was 100 mM HEPES-NaOH buffer, and the reaction system volume was 100 µL. The alditol oxidase (ScALDO-Q288G) in the reaction system was replaced with the same amount of wild-type alditol oxidase ScALDO, the concentration of other substances remained unchanged, and the reaction was carried out under the same conditions for 24 hours as a control group.

The concentration of pyruvic acid in the three-enzyme reaction system of alditol oxidase ScALDO-Q288G, dehydratase PuDHT and 2-keto-3-deoxy gluconate aldolase PtKDGA at different reaction times was determined, and the concentration of pyruvic acid in the reaction system of control group was determined.

Figure 3:
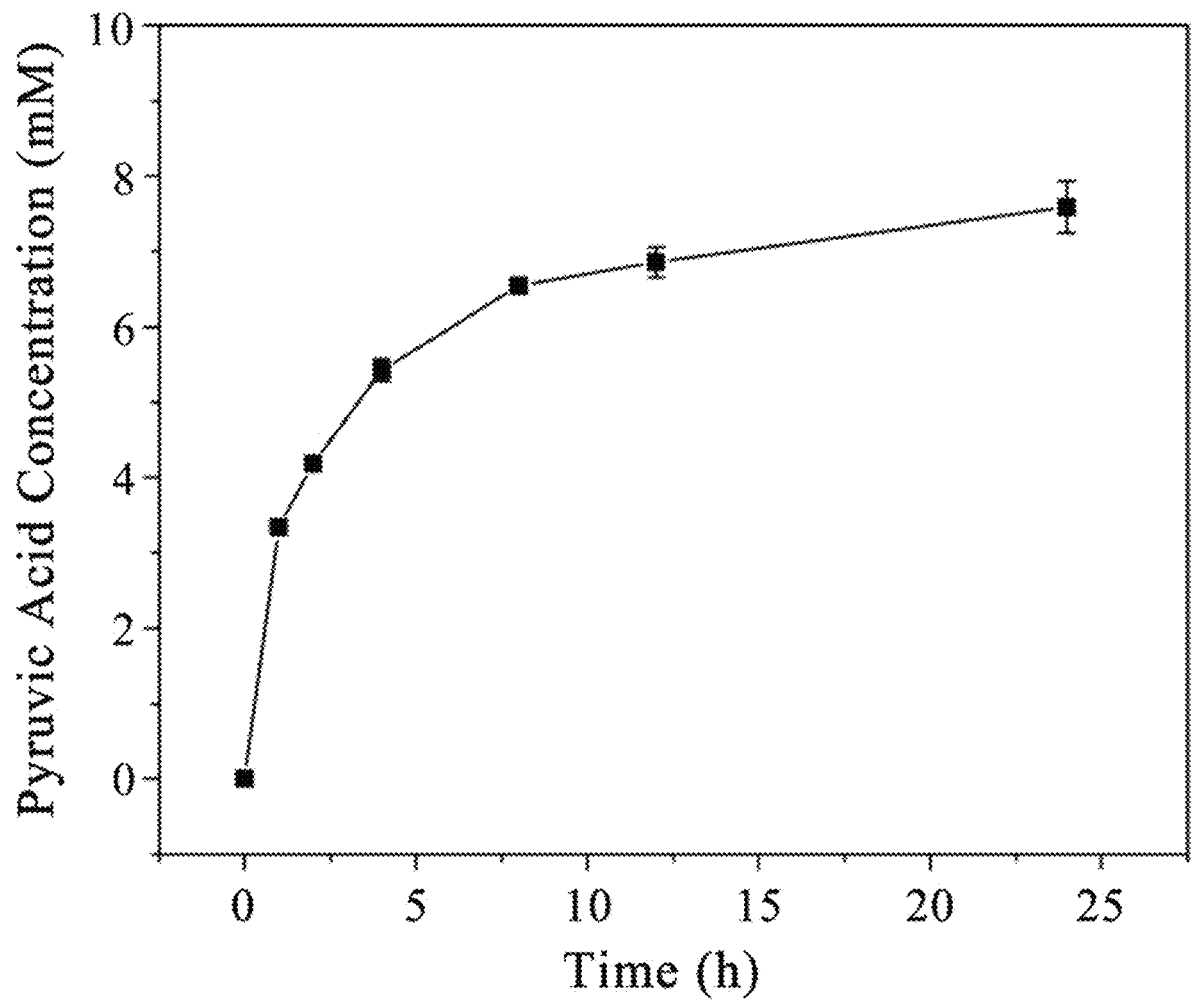
FIG. 3 is a concentration-time curve of the three-enzyme catalytic reaction of the alditol oxidase according to the present application using D-glucose as the substrate to synthesize pyruvic acid.

Referring to FIG. 3, it shows a concentration-time curve of the three-enzyme catalytic reaction for synthesizing pyruvic acid using D-glucose as a substrate. The three-enzyme reaction system of alditol oxidase ScALDO-Q288G, dehydratase PuDHT and 2-keto-3-deoxy gluconate aldolase PtKDGA may convert glucose into pyruvic acid, and the maximum conversion rate may reach 75.8%.

Figure 4:
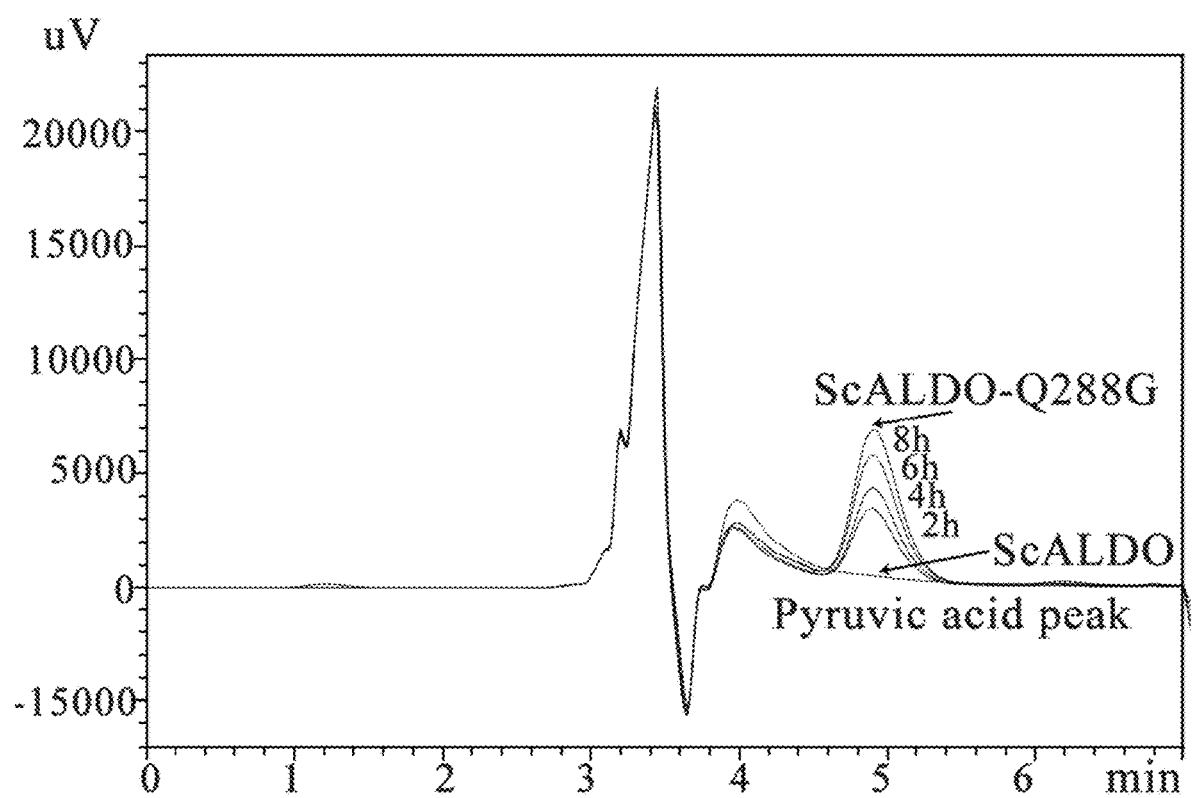
FIG. 4 is a liquid phase peak diagram of the three-enzyme catalytic reaction of the alditol oxidase according to the present application using D-glucose as the substrate to synthesize pyruvic acid.

Referring to FIG. 4, it shows a liquid phase peak diagram of the three-enzyme catalytic reaction for synthesizing pyruvic acid using D-glucose as the substrate. No pyruvic acid was produced in the reaction system of the control group, which further indicated that the alditol oxidase of the application has unique substrate promiscuity.

Figure 5:
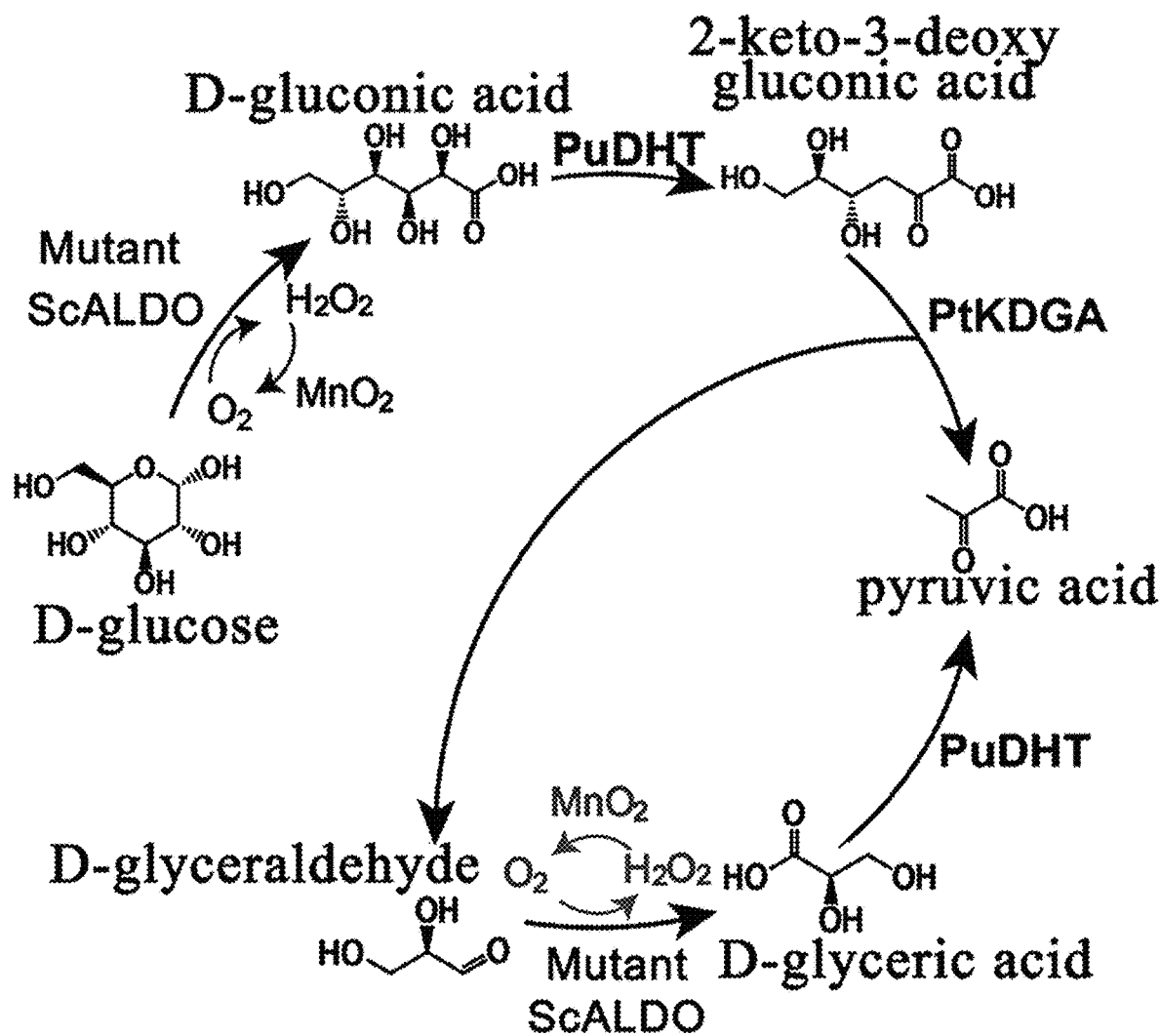
FIG. 5 is a reaction route of the three-enzyme catalytic reaction according to the present application using D-glucose as the substrate to synthesize pyruvic acid.

Referring to FIG. 1 and FIG. 5, the oxidation of D-glucose to D-gluconic acid and the oxidation of D-glyceraldehyde to D-glyceric acid were carried out by two enzymes, glucose dehydrogenase and glyceraldehyde dehydrogenase, respectively in all reports. In this embodiment, the reaction circuit of the three-enzyme catalytic reaction using the alditol oxidase of the application to synthesize pyruvic acid with D-glucose as the substrate was as follows: one molecule of D-glucose was converted into one molecule of D-gluconic acid catalyzed by alditol oxidase, and then one molecule of D-gluconic acid was converted to 2-keto-3-deoxy gluconic acid catalyzed by dehydratase PuDHT. Subsequently, 2-keto-3-deoxy gluconic acid was catalyzed by 2-keto-3-deoxy gluconate aldolase PtKDGA to convert to one molecule of D-glyceraldehyde and one molecule of pyruvic acid, one molecule of D-glyceraldehyde was catalyzed by alditol oxidase to convert to one molecule of D-glyceric acid, and one molecule of D-glyceric acid was catalyzed by dehydratase PuDHT to convert to another molecule of pyruvic acid. One molecule of glucose may theoretically be converted into two molecules of pyruvic acid. Compared with other studies, the glucose dehydrogenase (GDH) and glyceraldehyde dehydrogenase (ALDH) required for the synthesis of pyruvic acid from D-glucose were replaced by the alditol oxidase provided in the present application, and the number of enzymes required for the synthesis of pyruvic acid from D-glucose was reduced from four to three, and the dependence on cofactor NAD+ was eliminated.

Therefore, the present application provides an alditol oxidase ScALDO-Q288G and ScALDO-Q288A, which has a new property of simultaneously oxidizing D-glucose and D-glyceraldehyde, and may reduce the number of enzymes required for synthesizing pyruvate from D-glucose from 4 to 3 for the first time, and does not depend on any coenzyme, and has great originality and application value.

Example 7: Application of Mutant Alditol Oxidase in the Oxidation of Various Aldoses This embodiment tested the oxidation activity of wild-type and mutant alditol oxidases (ScALDO, ScALDO-Q288G, and ScALDO-Q288G) provided in the present application on various aldoses, including D-xylose, D-ribose, L-arabinose, D-erythrose, D-mannose, and D-galactose. In the process of oxidizing aldose, alditol oxidase will release $H_2O_2$, and the released $H_2O_2$ and 4-AAP, DHBS generated chromogenic substances under the catalysis of horseradish peroxidase. By detecting the generation of chromogenic substances at 515 nm wavelength, the oxidation activity of wild-type or mutant alditol oxidase on aldose was tested, and the relative enzyme activity was calculated when the highest enzyme activity defined as 100%.

Figure 6:
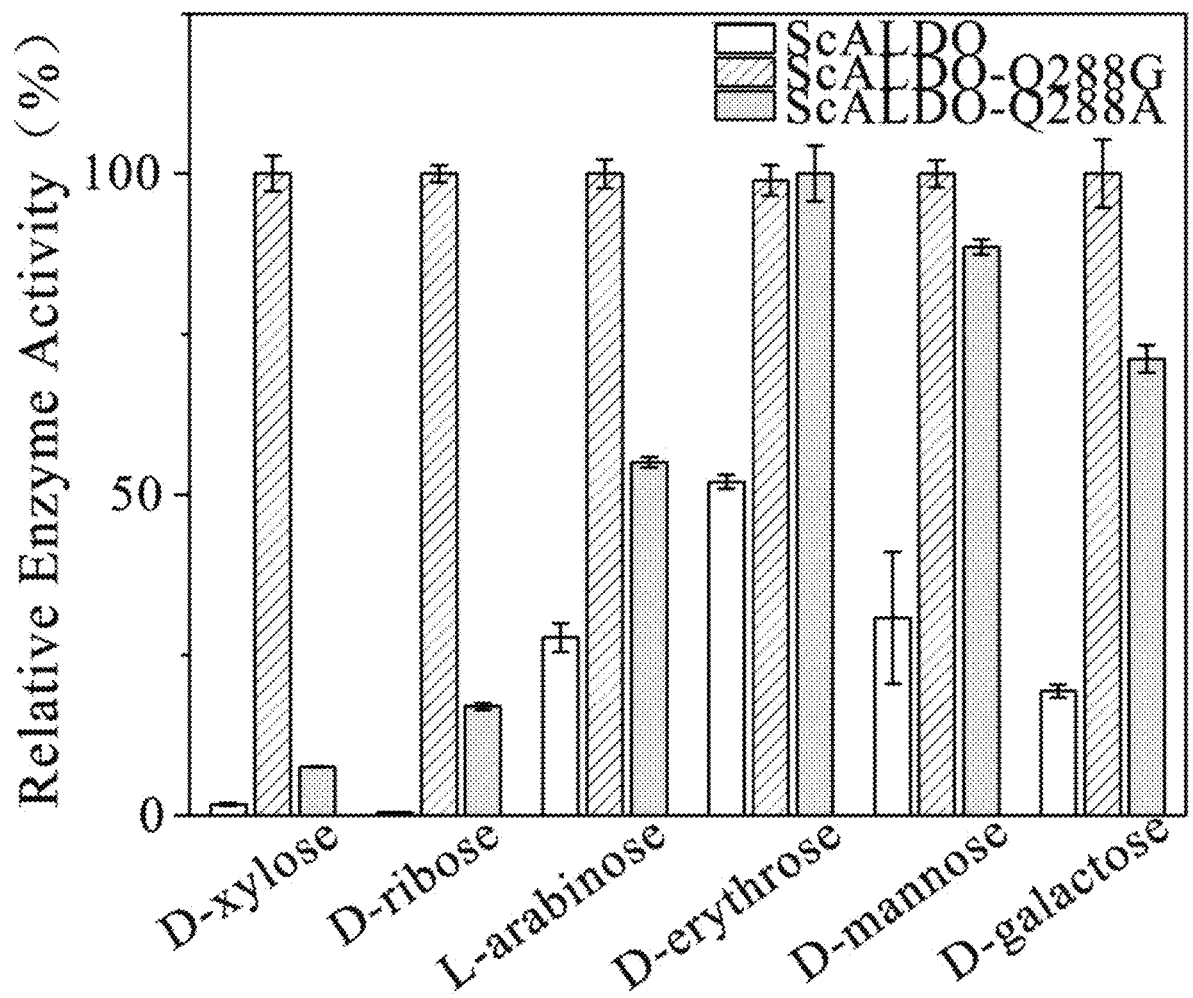
FIG. 6 shows relative enzyme activity of the alditol oxidase according to the present application for oxidizing different aldoses.

Referring to FIG. 6, it shows the relative enzyme activity of alditol oxidases (ScALDO-Q288G and ScALDO-Q288G) for oxidizing different aldoses. Compared with wild-type alditol oxidase ScALDO, the enzyme activity of alditol oxidase SCALDO-Q288G (SEQ ID NO: 2) provided in the present application was increased by 59 folds, and the enzyme activity of alditol oxidase ScALDO-Q288A (SEQ ID NO: 4) provided in the present application was increased by 4.4 folds when D-xylose was used as the substrate.

Compared with wild-type alditol oxidase ScALDO, the enzyme activity of alditol oxidase SCALDO-Q288G (SEQ ID NO:2) provided in the present application was increased by 226.3 folds, and the enzyme activity of alditol oxidase ScALDO-Q288A (SEQ ID NO:4) provided in the present application was increased by up to 38.3 folds when D-ribose was used as the substrate.

Compared with wild-type alditol oxidase ScALDO, the enzyme activity of alditol oxidase SCALDO-Q288G (SEQ ID NO:2) provided in the present application was increased by 3.61 folds, and the enzyme activity of alditol oxidase ScALDO-Q288A (SEQ ID NO:4) provided in the present application was increased by 1.98 folds when L-arabinose was used as the substrate.

Compared with wild-type alditol oxidase ScALDO, the enzyme activity of alditol oxidase SCALDO-Q288G (SEQ ID NO:2) provided in the present application was increased by 1.9 folds, and the enzyme activity of alditol oxidase ScALDO-Q288A (SEQ ID NO:4) provided in the present application was increased by 1.9 folds when D-erythrose was used as the substrate.

Compared with wild-type alditol oxidase ScALDO, the enzyme activity of alditol oxidase SCALDO-Q288G (SEQ ID NO:2) provided in the present application was increased by 3.2 folds, and the enzyme activity of alditol oxidase ScALDO-Q288A (SEQ ID NO:4) provided in the present application was increased by 2.9 folds when D-mannose was used as the substrate.

Compared with wild-type alditol oxidase ScALDO, the enzyme activity of alditol oxidase SCALDO-Q288G (SEQ ID NO:2) provided in the present application was increased by 5.1 folds, and the enzyme activity of alditol oxidase ScALDO-Q288A (SEQ ID NO:4) provided in the present application was increased by 3.7 folds when D-galactose was used as the substrate.

The above embodiments are only a description of the preferred embodiments of the present invention, and do not limit the scope of the present invention. Without departing from the design spirit of the present invention, various modifications and changes made by ordinary skill person in the art to the technical solutions of the present invention should fall within the protection scope determined by claims of the present invention.

What is claimed:

1. An alditol oxidase comprising the amino acid sequence as shown in SEQ ID NO: 2 or the amino acid sequence as shown in SEQ ID NO: 4.

2. A gene encoding the alditol oxidase of claim 1.

3. The gene of claim 2, wherein the gene comprises the nucleotide sequence as shown in SEQ ID NO: 3 or the nucleotide sequence as shown in SEQ ID NO: 5.

4. A recombinant vector comprising the gene of claim 2.

5. The recombinant vector of claim 4, wherein the recombinant vector comprises pET28a as an expression vector.

6. A recombinant strain comprising the gene of claim 2.

7. The recombinant strain of claim 6, wherein the recombinant strain is *Escherichia coli* BL21 (DE3) as a host.

8. A method for synthesizing pyruvic acid, comprising catalyzing conversion of D-glucose as a substrate to pyruvic acid in a reaction system comprising D-glucose, the aldol oxidase of claim 1, a dehydratase, and a 2-keto-3-deoxy gluconate aldolase.

9. The method of claim 8, wherein a concentration of the alditol oxidase is 0.3 to 0.7 mg/mL, a concentration of the dehydratase is 0.3 to 0.5 mg/mL, and a concentration of the 2-keto-3-deoxy gluconate aldolase is 0.1 to 0.3 mg/mL in the reaction system.

10. The method of claim 9, the reaction system further comprises $MgCl_2$ and manganese dioxide, wherein reaction temperature of the reaction system is 38 to 42° C.

11. A method for oxidation of an aldose, comprising catalyzing an oxidation reaction of an aldose in the presence of the alditol oxidase of claim 1, wherein the aldose is selected from the group consisting of D-xylose, D-ribose, L-arabinose, D-erythrose, D-mannose and D-galactose.

* * * * *